(12) United States Patent
Brain

(10) Patent No.: US 7,134,431 B2
(45) Date of Patent: Nov. 14, 2006

(54) LARYNGEAL MASK AIRWAY DEVICE WITH POSITION CONTROLLING TAB

(75) Inventor: Archibald I. J. Brain, Mahe (SC)

(73) Assignee: Indian Ocean Medical Inc., Mahe (SC)

( * ) Notice: Subject to any disclaimer, the term of this patent is extended or adjusted under 35 U.S.C. 154(b) by 223 days.

(21) Appl. No.: 10/657,418

(22) Filed: Sep. 8, 2003

(65) Prior Publication Data
US 2005/0051173 A1    Mar. 10, 2005

(51) Int. Cl.
*A61M 16/00*    (2006.01)

(52) U.S. Cl. ............................. 128/200.26; 128/207.14

(58) Field of Classification Search ........... 128/200.26, 128/207.14, 207.15, 207.16; 604/100.01, 604/102.01, 102.02, 102.03
See application file for complete search history.

(56) References Cited

U.S. PATENT DOCUMENTS

| | | | |
|---|---|---|---|
| 2,862,498 A | 12/1958 | Weekes | |
| 3,554,673 A | 1/1971 | Schwartz et al. | |
| 4,231,365 A | 11/1980 | Scarberry | |
| 4,509,514 A | 4/1985 | Brain | |
| 4,553,540 A | 11/1985 | Straith | |
| 4,793,327 A * | 12/1988 | Frankel | 600/194 |
| 4,872,483 A | 10/1989 | Shah | |
| 4,953,547 A | 9/1990 | Poole, Jr. | |
| 4,995,388 A | 2/1991 | Brain | |
| 5,038,766 A | 8/1991 | Parker | |
| 5,241,956 A | 9/1993 | Brain | |
| 5,249,571 A | 10/1993 | Brain | |
| 5,277,178 A * | 1/1994 | Dingley | 128/200.26 |
| 5,282,464 A | 2/1994 | Brain | |
| 5,297,547 A * | 3/1994 | Brain | 128/207.15 |
| 5,303,697 A * | 4/1994 | Brain | 128/200.26 |

(Continued)

FOREIGN PATENT DOCUMENTS

CA    2067782    6/1999

(Continued)

OTHER PUBLICATIONS

Abdelatti, "A cuff pressure controller for tracheal tubes and laryngeal mask airway," *Anaesthesia*, 1999, 54 pp. 981-986.

(Continued)

*Primary Examiner*—Teena Mitchell
(74) *Attorney, Agent, or Firm*—Wilmer Cuter Pickering Hale and Dorr LLP

(57) ABSTRACT

The disclosed laryngeal mask airway device includes an inflatable cuff, an airway tube, and a tab. The cuff defines a central opening at least when inflated. The cuff is insertable through a mouth of a patient to an inserted location within the patient. The cuff surrounds a glottic opening of the patient when inflated and at the inserted location. The airway tube extends from a proximal end to a distal end. The airway tube defines an internal passage. A sealed airway passage extends from the proximal end of the tube through the internal passage to the glottic opening when the cuff is inflated and at the inserted location. The tab is fixed to the airway tube near the proximal end of the airway tube. The tab is disposed outside of the mouth of the patient when the cuff is at the inserted location. The tab extends outwardly from the airway tube in a first direction when the cuff is at the inserted location. A second direction is perpendicular to a line extending from a nose of the patient to a chin of the patient. The first direction is transverse to the second direction.

30 Claims, 11 Drawing Sheets

U.S. PATENT DOCUMENTS

| | | | |
|---|---|---|---|
| 5,339,805 A | 8/1994 | Parker | |
| 5,339,808 A | 8/1994 | Don Michael | |
| 5,355,879 A | 10/1994 | Brain | |
| 5,391,248 A | 2/1995 | Brain | |
| 5,529,582 A | 6/1996 | Fukuhara | |
| 5,569,219 A | 10/1996 | Hakki et al. | |
| 5,584,290 A | 12/1996 | Brain | |
| 5,599,301 A | 2/1997 | Jacobs et al. | |
| 5,623,921 A * | 4/1997 | Kinsinger et al. | 128/200.26 |
| 5,632,271 A | 5/1997 | Brain | |
| RE35,531 E | 6/1997 | Callaghan et al. | |
| 5,653,229 A | 8/1997 | Greenberg | |
| 5,655,528 A | 8/1997 | Pagan | |
| 5,682,880 A * | 11/1997 | Brain | 128/207.15 |
| 5,711,293 A | 1/1998 | Brain | |
| 5,743,254 A | 4/1998 | Parker | |
| 5,746,202 A | 5/1998 | Pagan | |
| 5,771,889 A * | 6/1998 | Pagan | 128/207.15 |
| 5,791,341 A * | 8/1998 | Bullard | 128/207.15 |
| 5,850,832 A | 12/1998 | Chu | |
| 5,865,176 A * | 2/1999 | O'Neil | 128/207.15 |
| 5,878,745 A * | 3/1999 | Brain | 128/207.15 |
| 5,881,726 A | 3/1999 | Neame | |
| 5,896,858 A * | 4/1999 | Brain | 128/207.15 |
| 5,915,383 A | 6/1999 | Pagan | |
| 5,937,860 A | 8/1999 | Cook | |
| 5,979,445 A | 11/1999 | Neame et al. | |
| 5,983,897 A | 11/1999 | Pagan | |
| 5,988,167 A | 11/1999 | Kamen | |
| 6,003,510 A | 12/1999 | Anunta | |
| 6,003,514 A | 12/1999 | Pagan | |
| 6,012,452 A | 1/2000 | Pagan | |
| 6,021,779 A | 2/2000 | Pagan | |
| 6,050,264 A | 4/2000 | Greenfield | |
| 6,070,581 A | 6/2000 | Augustine et al. | |
| 6,079,409 A | 6/2000 | Brain | |
| D429,811 S | 8/2000 | Bermudez | |
| 6,095,144 A | 8/2000 | Pagan | |
| 6,116,243 A | 9/2000 | Pagan | |
| 6,119,695 A | 9/2000 | Augustine et al. | |
| 6,390,093 B1 | 5/2002 | Mongeon | |
| 6,427,686 B1 * | 8/2002 | Augustine et al. | 128/200.26 |
| 2003/0131845 A1 * | 7/2003 | Lin | 128/200.26 |

FOREIGN PATENT DOCUMENTS

| | | |
|---|---|---|
| CA | 2012750 | 8/1999 |
| EP | 0 389 272 | 9/1990 |
| EP | 0 402 872 | 12/1990 |
| EP | 0 294 200 | 4/1992 |
| EP | 0 580 385 | 5/1996 |
| EP | 0 712 638 | 5/1996 |
| EP | 0 732 116 | 9/1996 |
| EP | 0 796 631 | 9/1997 |
| EP | 0 845 276 | 6/1998 |
| EP | 0 865 798 | 9/1998 |
| EP | 0 922 465 | 6/1999 |
| EP | 1 125 595 | 8/2001 |
| GB | 2111394 | 12/1982 |
| GB | 2205499 | 6/1987 |
| GB | 2317342 | 8/1997 |
| GB | 2317830 | 9/1997 |
| GB | 2318735 | 10/1997 |
| GB | 2319478 | 10/1997 |
| GB | 2321854 | 1/1998 |
| GB | 2323289 | 2/1998 |
| GB | 2323290 | 3/1998 |
| GB | 2323291 | 3/1998 |
| GB | 2323292 | 3/1998 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO 91/03207 | 3/1991 |
| WO | WO 91/07201 | 5/1991 |
| WO | WO 91/12845 | 9/1991 |
| WO | WO 92/13587 | 8/1992 |
| WO | WO 95/33506 | 12/1995 |
| WO | WO 97/12640 | 4/1997 |
| WO | WO 97/12641 | 4/1997 |
| WO | WO 98/16273 | 4/1998 |
| WO | WO 99/06093 | 2/1999 |
| WO | WO 00/22985 | 4/2000 |
| WO | WO 00/23135 | 4/2000 |
| WO | WO 00/61212 | 10/2000 |

OTHER PUBLICATIONS

Benumof J.L. "Management of the difficult airway with special emphasis on awake tracheal intubation," *Anesthesiol.* 1991. 75;6:1087.

Benumof, "Laryngeal Mask Airway and the ASA Difficult Airway Algorithm," *Anesthesiology* 1996:v84 No. 3:686-99.

Bernhard, et al., "Adjustment of Intracuff Pressure to Prevent Aspiration," *Anesthesiology* v. 50 No. 4:363-366, 1979.

Bernhard, et al., "Physical Characteristics of and Rates of Nitrous Oxide Diffusion into Tracheal Tube Cuffs," *Anesthesiology* 48:413-417 1978.

Brain, "The Laryngeal Mask—A New Concept in Airway Management," *Br. J. Anesth.* (1983), vol. 55, pp. 801-805.

Brain, "The laryngeal mask airway -a possible new solution to airway problems in the emergency situation," *Archives of Emergency Medicine*, 1984, 1, 229-232.

Brain, "The laryngeal mask airway," *Anaesthesia*, 1985, vol. 40, pp. 356-361.

Brain, "Three cases of difficult intubation overcome by the laryngeal mask airway," *Anaesthesia*, 1985, vol. 40, pp. 353-355.

Brain, et al., "A new laryngeal mask prototype," *Anaesthesia*, 1995, vol. 50, pp. 42-48.

Brimacombe, "The split laryngeal mask airway," p. 639.

Broderick, "The laryngeal mask airway," (1989) *Anaesthesia*, vol. 44, pp. 238-241.

Burgard, et al., The Effect of Laryngeal Mask Cuff Pressure on Postoperative Sore Throat Incidence, *J. of Clinical Anesthesia* 8:198-201, 1996.

Caplan R.A., Posner K.L., Wend R.J., Cheney F.W., "Adverse respiratory events in anesthesia: a closed claims analysis", *Anesthesiol.* 1990. 72:828-833.

Craven, "Prevention of Hospital-Acquired Pneumonia: Measuring Effect in Ounces, Pounds, and Tons," *Annals of Internal Medicine*, vol. 122, No. 3, pp. 229-231 Feb. 1, 1995.

Cuff-Pressure-Control CDR 2000, LogoMed.

Davies, et. al., "Laryngeal mask airway and tracheal tube insertion by unskilled personnel," *The Lancet*, vol. 336, pp. 977-979.

DeMello, et al., "The use of the laryngeal mask airway in primary anaesthesia," *Anaesth. Corresp.* (1990) 45,9:793.

Doyle et al., "Intraoperative Awareness: A Continuing Clinical Problem," http://doyle.ibme.utoronto.ca/anesthesia/aware.htm.

Engbers, "Practical use of 'Diprifusor' systems", *Anaesthesia* 1998, 53, Suppl. 1, pp. 28-34.

Eriksson, et al., "Functional Assessment of the Pharynx at Rest and during Swallowing in Partially Paralyzed Humans," *Anesthesiology* vol. 87, No. 5, Nov. 1997, pp. 1035-1042.

Glen, "The development of 'Diprifusor': a TCI system for propofol," *Anaesthesia* 1998, 53, Suppl. 1, pp. 13-21.

Gray et al., "Development of the technology for 'Diprifusor' TCI systems," *Anaesthesia* 1998, 53, Suppl. 1, pp. 22-27.

Heath, "Endotracheal intubation through the Laryngeal Mask—helpful when laryngoscopy is difficult or dangerous," *European Journal of Anaesthesiology* 1991, Suppl. 4, 41-45.

Hickey, et al., "Cardiovascular response to insertion of Brain's laryngeal mark," *Anesth. Corresp.* 1990, vol. 45 pp. 629-633.

Inomata, et al., "Transient Bilateral Vocal Cord Paralysis after Insertion of a Laryngeal Mask Airway," *Anesthesiology*, 82:787-788, 1995.

Jacobson et al., A Study of Intracuff Pressure Measurements, Trends and Behaviours in Patients During Prolonged Periods of Tracheal Intubation, *Br. J. Anaesth.* 1981, 53, 97.

Kambic, et al., "Intubation Lesions of the Larynx," *Br. J. Anasth.* 1978, 50, 587-590.

Kapila A., Addy E.V., Verghese C., Brain A.J., "Intubating LMA: a preliminary assessment of performance", *British Journal of Anaesthesia*, 1995; 75:228-229 (Abstract).

Lindholm, "Prolonged Endotracheal Intubation," *ACTA Anaesthesiologica Scandinavica* 1969 vol. 33 32-46.

Majumder, et al., "Bilateral Lingual Nerve Injury Following the Use of the Laryngeal Mask Airway," *Anaesthesia*, 1998, vol. 53, pp. 184-186.

Miller, "A pressure regulator for the cuff of a tracheal tube," *Anaesthesia*, 1992, vol. 47, pp. 594-596.

Muthuswamy, et al., "The Use of Fuzzy Integrals and Bispectral Analysis of the Electroencephalogram to Predict Movement Under Anesthesia," *IEEE Transactions on Biomedical Engineering*, vol. 46, No. 3, Mar. 1999, pp. 290-299.

Nagai, "Unilateral hypoglossal nerve paralysis following the use of the laryngeal mask airway," *Anaesthesia*, 1994, vol. 49, pp. 603-604.

Patel, et al., "Trachael tube cuff pressure," *Anaesthesia*, 1984, vol. 39, pp. 862-864.

Pennant, "Comparison of the Endotracheal Tube and Laryngeal Mask in Airway Management by Paramedical Personnel," *Anesth Analg* 1992:74:531-4.

Pippin, et al., "Long-term tracheal intubation practice in the United Kingdom", *Anaesthesia*, 1983, vol. 38, pp. 791-795.

Raeder, et al., "Tracheal tube cuff pressures," *Anaesthesia*, 1985, vol. 40, pp. 444-447.

Seegobin, et al., "Endotracheal cuff pressure and tracheal mucosal blood flow: endoscopic study of effects of four large volume cuffs," *British Medical Journal*, vol. 288, Mar. 31, 1984.

Willis, et al., "Tracheal tube cuff pressure," *Anaesthesia*, 1988, vol. 43, pp. 312-314.

Worthington, et al., "Proceedings of the Anaesthetic Research Society," *Br. J. of Anaesthesia* 1995 75:228P-229P.

Wynn, et al., "Tongue Cyanosis after Laryngeal Mask Airway Insertion," *Anesthesiology*, V. 80, No. 6, Jun. 1994, p. 1403.

\* cited by examiner

LARYNGEAL MASK AIRWAY DEVICE WITH POSITION CONTROLLING TAB

BACKGROUND OF THE INVENTION

The present invention relates to a laryngeal mask airway device. More specifically, the present invention relates to a laryngeal mask airway device having a tab disposed near the device's proximal end for facilitating position control of the device.

The laryngeal mask airway device is a well known device that is useful for establishing airways in unconscious patients. One popular laryngeal mask airway device has been marketed commercially for many yeas as the "Classic" by the Laryngeal Mask Company of Cyprus. Such devices are described for example in U.S. Pat. No. 4,509,514. The Classic is a reusable device and is guaranteed to survive at least forty sterilizations, and in practice these devices may generally be sterilized (and reused) more than forty times before becoming too worn for reuse. In recent years, attempts have been made to develop reduced cost, disposable, laryngeal mask airway devices. U.S. patent application Ser. Nos. 09/544,681 and 10/138,806, which name the inventor of the present application, describe several embodiments of disposable laryngeal mask airway devices.

FIGS. 1A, 1B, and 1C show various views of a prior art disposable laryngeal mask airway device 100 when the cuff is inflated. FIG. 2 shows a partially sectional side view of device 100 when inserted into a patient. Referring to FIG. 1A, device 100 includes an airway tube 110 and a mask portion 130. Mask portion 130 includes a flat plate 132 and an inflatable cuff 134. Mask portion 130 extends from a proximal end 136 to a distal end 138. Mask portion 130 is attached to a distal portion 112 of airway tube 110. Device 100 also includes an inflation line 190 (shown in FIG. 1B) and a check valve 192 for selectively inflating and deflating cuff 134.

In operation, cuff 134 is deflated, and the mask portion is then inserted through the patient's mouth into the patient's pharynx. The device is preferably positioned so that distal end 138 of mask portion 130 rests against the patient's normally closed esophagus and so that the open end 140 (shown in FIG. 1C) of mask portion 130 is aligned with the entryway of the patient's trachea (i.e., the patient's glottic opening). After the mask portion is so positioned, the cuff is inflated and forms a seal around the patient's glottic opening and thus establishes a sealed airway extending from a proximal end 114 of airway tube 110 to the patient's trachea.

For convenience of exposition, the term "fully inserted configuration" shall be used herein to refer to a laryngeal mask airway device that has been inserted into a patient and has the following characteristics: (1) the distal end of the mask portion is pressed against the patient's normally closed esophageal sphincter; (2) the cuff is inflated and forms a seal around the patient's glottic opening; and (3) the airway tube extends from a proximal end located outside the patient's mouth to a distal portion that is coupled to the mask portion, the tube extending through the patient's mouth and the patient's natural upper airway so that the device provides a sealed airway extending from the tube's proximal end to the patient's lungs.

FIG. 2 shows a laryngeal mask airway device 100 in the fully inserted configuration. As shown, the distal end of the mask portion 130 is pressed against the patient's esophageal sphincter 210. Also, the open end of the mask portion forms a seal around the glottic opening 212 thereby enabling the device 100 to provide fluid communication with the trachea 214.

Although prior art disposable laryngeal mask airway devices have performed well, there remains a need for providing improved devices. In particular, there remains a need for providing a disposable laryngeal mask airway device that more reliably remains stably in the fully inserted configuration once the device has been inserted into a patient.

SUMMARY OF THE INVENTION

These and other objects are provided by an improved disposable laryngeal mask airway device. The device may include a tab disposed near the proximal end of the airway tube. When the device is inserted into a patient, the tab is disposed near the patient's upper lip. The tab is conveniently located so that adhesive tape may be attached to the tab and the patient's cheeks. The tape applies a force that biases the device generally into the patient and, in particular, biases the distal end of the device against the patient's esophageal sphincter. This allows the device to remain more stably in the fully inserted configuration and reduces the likelihood that regurgitated material will be aspirated into the patient's lungs. The device may also include a flange in the inflatable cuff for supporting the epiglottis and preventing the epiglottis from blocking the airway passage provided by the device.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein:

FIG. 4E shows a cross sectional view of the integral tube and backplate portion taken along the line 4E—4E as shown in FIG. 4A.

DETAILED DESCRIPTION OF THE INVENTION

Figure 3A:
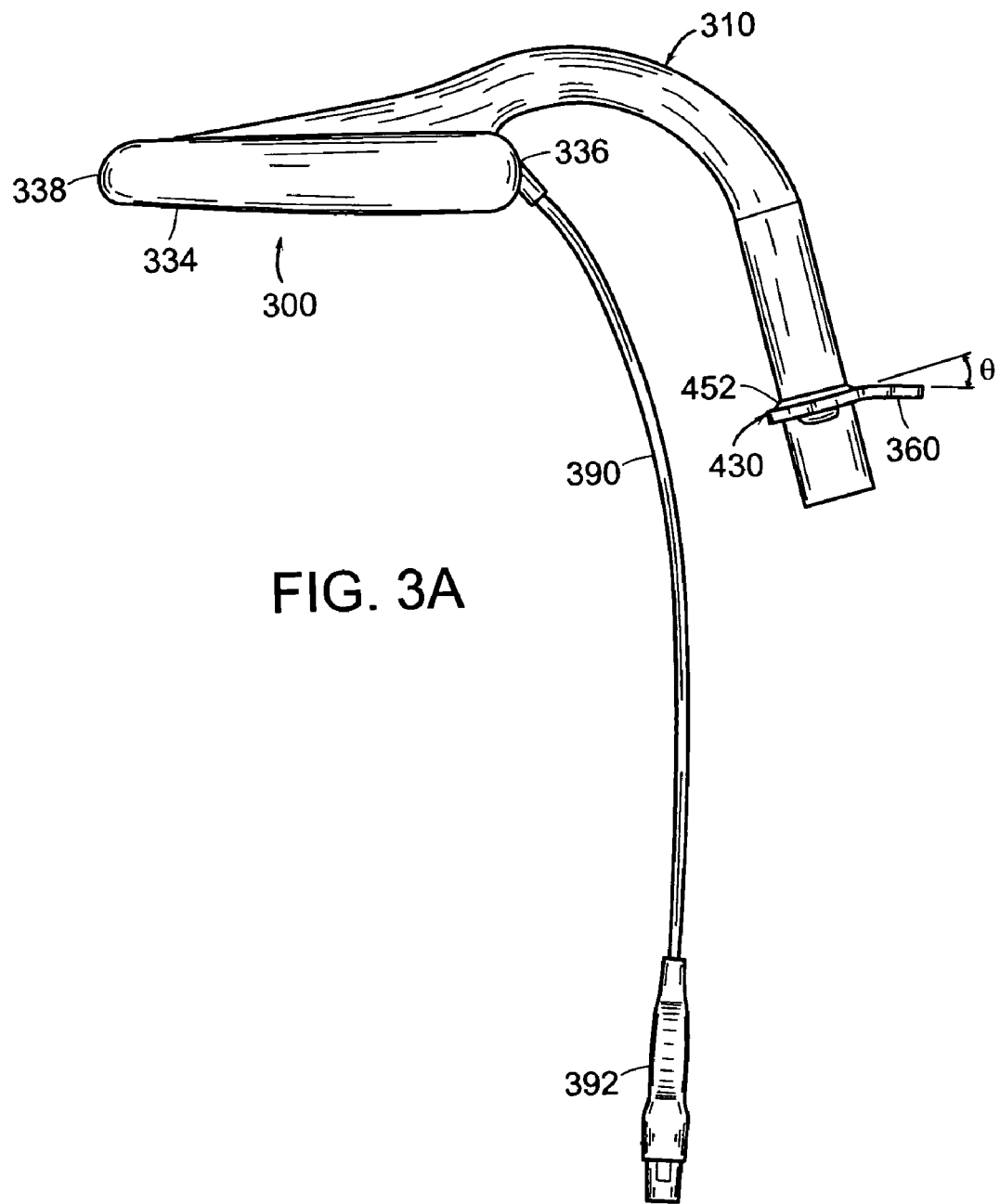
FIG. 3A shows a side view of a disposable laryngeal mask airway device constructed according to the invention when the cuff is inflated.
Figure 3B:
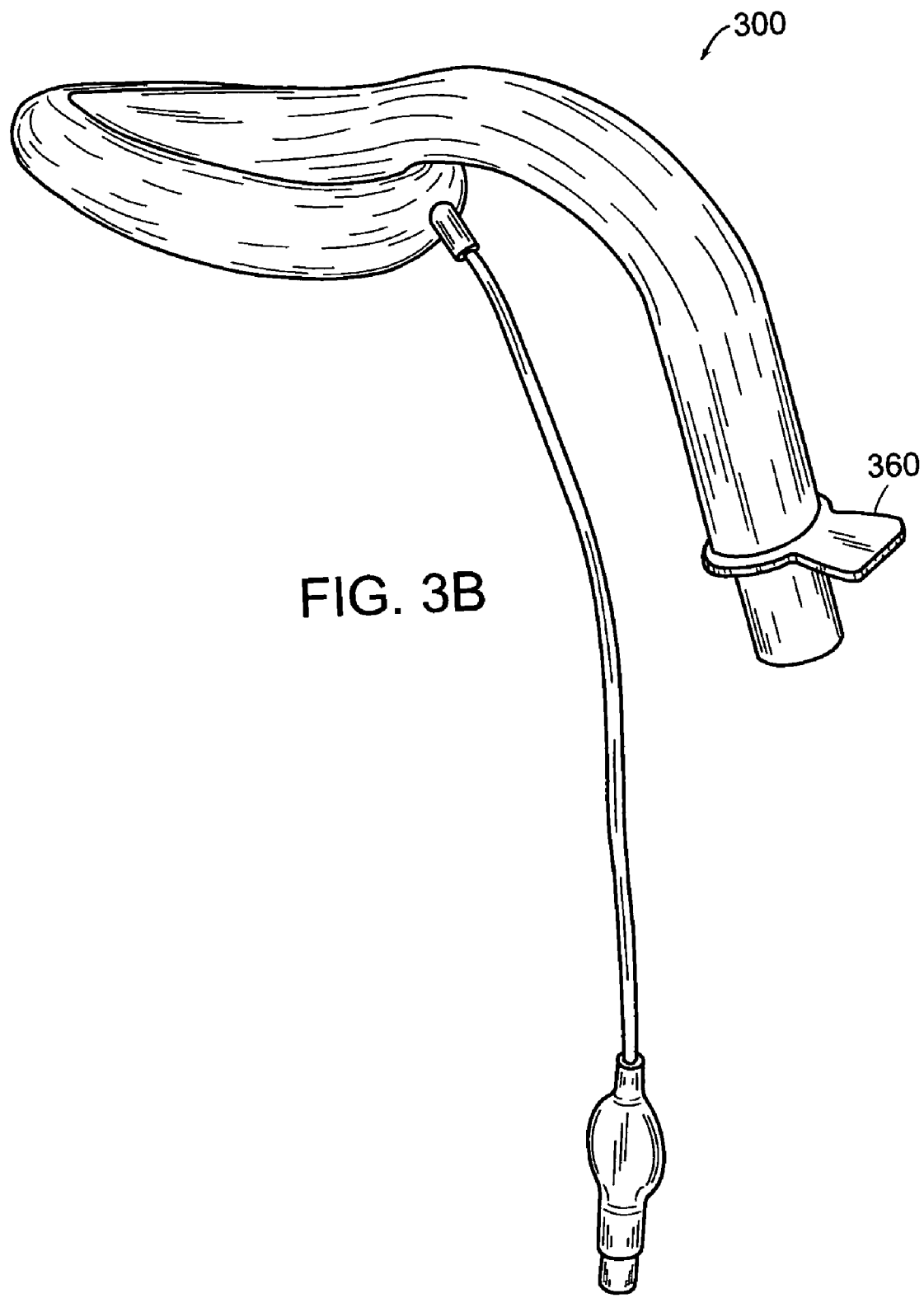
FIG. 3B shows a perspective view of the posterior side of the device shown in FIG. 3A.

FIGS. 3A and 3B show side and perspective views, respectively, of an improved disposable laryngeal mask airway device 300 constructed according to the invention. Device 300 includes an airway tube 310 and an inflatable cuff 334. The cuff 334 extends from a proximal end 336 to a distal end 338. Device 300 includes an inflation line 390, coupled to proximal end 336 of cuff 334, and a check valve 392 for selectively inflating and deflating cuff 334. Device 300 also includes a tab 360, which is integrally attached to airway tube 310. As will be discussed further below, tab 360 advantageously facilitates maintaining device 300 stably in the fully inserted configuration.

Figure 4A:
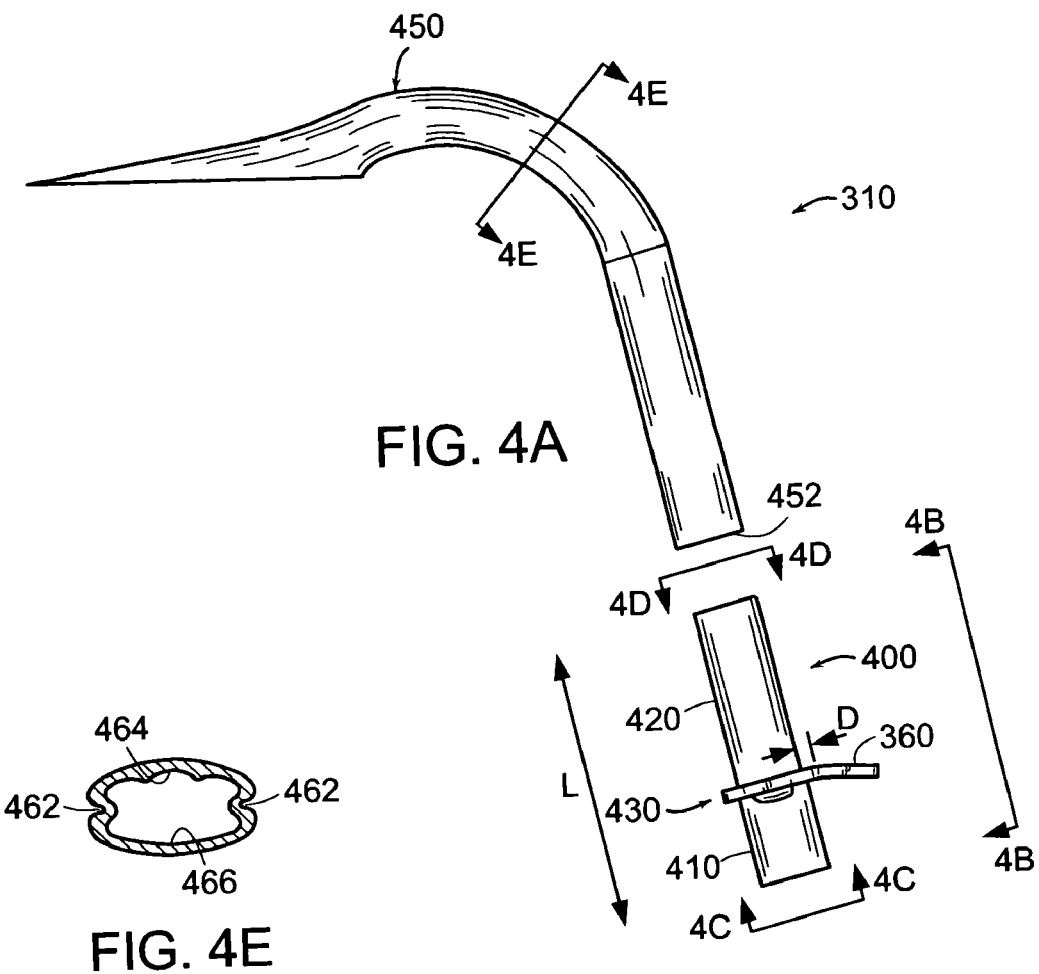
FIG. 4A shows an exploded side view of the airway tube of the device shown in FIGS. 3A and 3B.
Figure 4B:
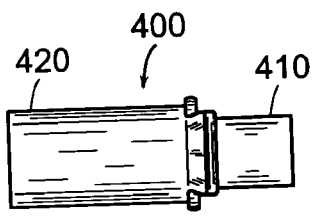
FIG. 4B shows a top view of the connector portion of the airway tube taken in the direction of arrow 4B—4B as shown in FIG. 4A.
Figure 4D:
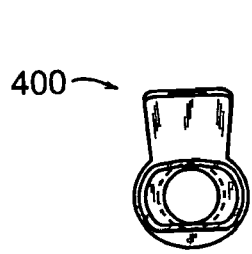
FIGS. 4C and 4D show end views of the connector portion of the airway tube taken in the direction of arrows 4C—4C and 4D—4D, respectively, as shown in FIG. 4A.
Figure 4C:
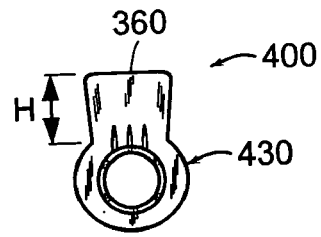

FIG. 4A shows an exploded side view of airway tube 310 prior to attachment of cuff 334. As shown, airway tube 310 includes a connector portion 400 and an integral tube and backplate portion 450. FIGS. 4B, 4C and 4D show views of connector portion 400 taken in the direction of arrows 4B—4B, 4C—4C, and 4D—4D, respectively, as shown in FIG. 4A.

Connector portion 400 includes a proximal portion 410, a distal portion 420, and a flange 430 located between the proximal and distal portions 410, 420. Tab 360 is formed as an integral part of flange 430. Proximal portion 410 is cylindrical and is configured to couple to standard medical ventilating, or anesthetic devices. Distal portion 420 is oblong and is configured for telescopic insertion into a proximal end 452 of integral tube and backplate portion 450. Airway tube 310 is assembled by telescopically inserting distal portion 420 into the proximal end 452 of integral tube and backplate portion 450 until flange 430 contacts proximal end 452 as shown in FIG. 3A. Connector portion 400 is made of a rigid plastic or polycarbonate material. Connector portion 400 can be made, for example, by injection molding. Connector portion 400 is preferably a single monolithic piece that defines proximal portion 410, distal portion 420, flange 430, and tab 360. Flange 430 and tab 360 are preferably rigid, and are preferably rigidly fixed relative to the rest of connector portion 400. Integral tube and backplate portion 450 is also made of a plastic material such as PVC and is softer than connector portion 400. Integral tube and backplate portion 450 is characterized by a durometer of about 90 on the Shore A scale of hardness. Integral tube and backplate portion 450 may also be made by injection molding and is preferably a single monolithic piece.

Figure 5:
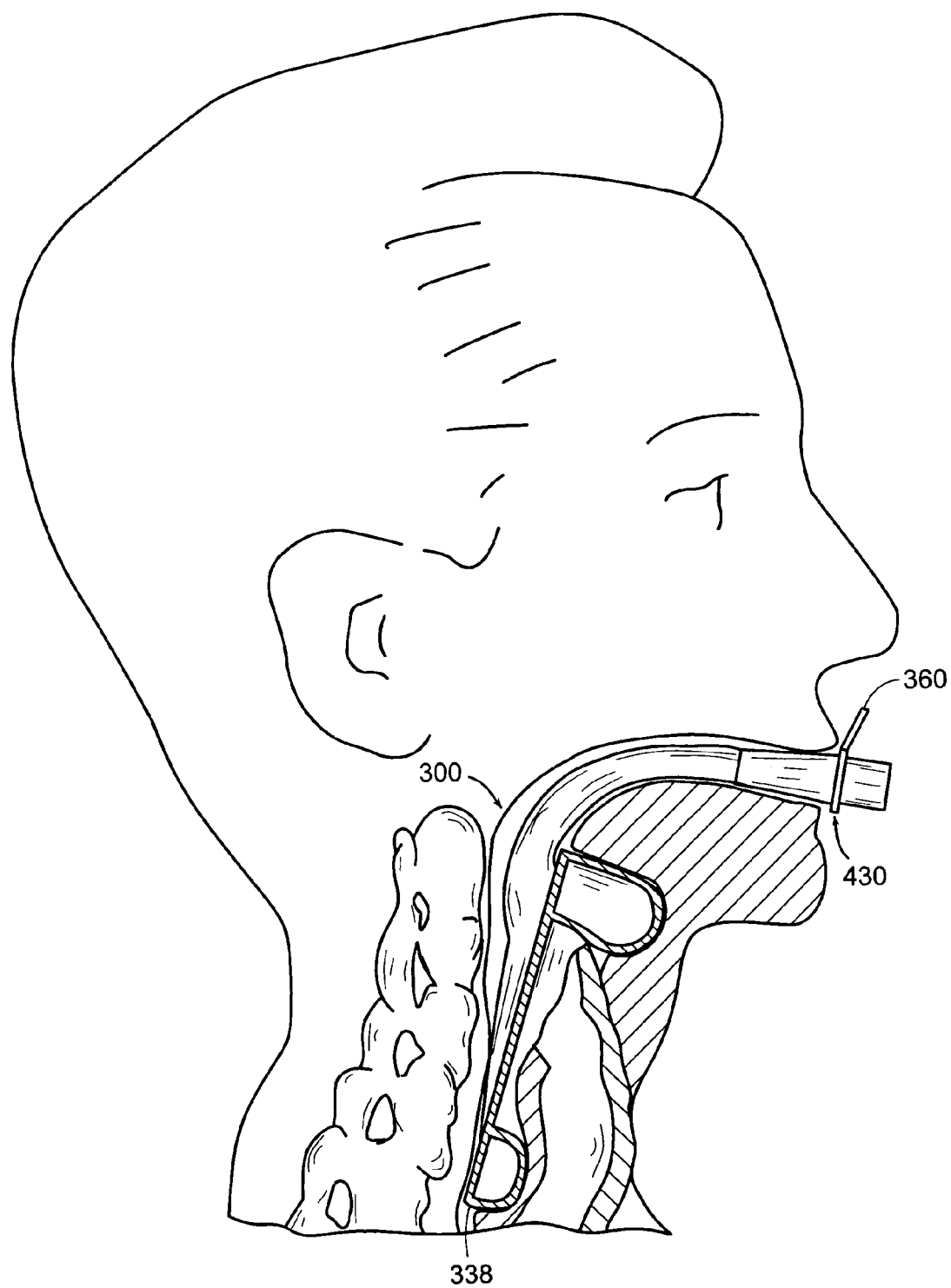
FIG. 5 shows a partially sectional side view of a disposable laryngeal mask airway device constructed according to the invention when in the fully inserted configuration.

FIG. 5 shows a view of device 300 in the fully inserted configuration. As shown, when device 300 is in the fully inserted configuration, tab 360 is disposed near the patient's upper lip. More specifically, the structure defined by flange 430 and tab 360 extends from the connector portion 400 of the airway tube past the bottom surface of the patient's upper lip towards the patient's nose, and tab 360 is generally proximal to the patient's upper lip. As will be discussed further below, locating tab 360 in this position when device 300 is inserted into a patient advantageously facilitates maintaining device 300 stably in the fully inserted configuration.

One problem with prior art disposable laryngeal mask airway devices is that they sometimes do not remain stably in the fully inserted configuration. In particular, in prior art devices it is difficult to insure that the distal tip of the device remains pressed against the patient's normally closed esophageal sphincter. Tab 360 advantageously facilitates maintaining device 300 stably in the fully inserted configuration, and, in particular, in maintaining firm contact between the distal end 338 of cuff 334 and the patient's normally closed esophageal sphincter.

Figure 6:
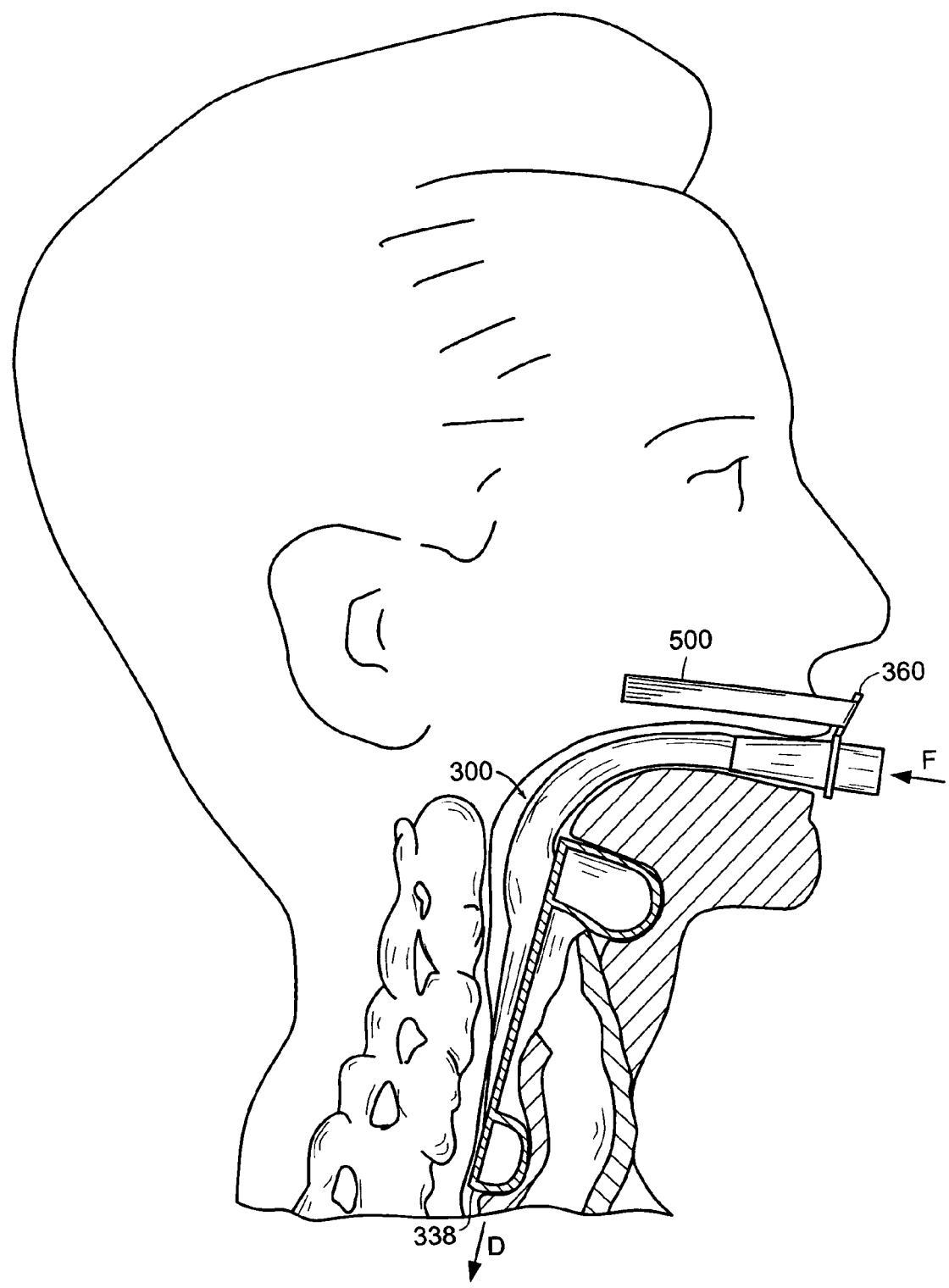
FIG. 6 shows a partially sectional side view of a disposable laryngeal mask airway device constructed according to the invention when adhesive tape has been applied to the tab and to the patient's cheeks to help maintain the device stably in the fully inserted configuration.

As shown in FIG. 6, once device 300 is inserted into a patient, a strip of adhesive tape 500 may be attached to tab 360 and the patient's cheeks. Tape 500 preferably extends from tab 360 generally towards the patient's ears as shown in FIG. 6. Once tape 500 is attached to tab 360 and the patient's cheeks, the tape 500 applies a force to tab 360 generally in the direction of the arrow F shown in FIG. 6. Airway tube 310 translates this force from tab 360 to the distal end of the device. The force applied by tape 500 acts to generally pull device 300 into the patient and, in particular, to simultaneously bias (a) the tab towards the patient's mouth and (b) the distal end of the device in the direction indicated by the arrow D in FIG. 6. Biasing the distal end of the device in the direction of the arrow D advantageously insures that the distal end 338 of cuff 334 remains generally in firm contact with the patient's normally closed esophageal sphincter. Insuring that the distal end of device 300 remains in firm contact with the patient's esophageal sphincter advantageously reduces the likelihood of regurgitated material being aspirated into the patient's lungs during anesthesia.

FIGS. 5 and 6 show the position of the tab 360 with respect to the patient's head and upper lip when the device is inserted in a "normal" patient. However, the size and shape of patient's airway passages can vary somewhat unpredictably such that in some patients the tab may actually contact the upper lip and in other patients the tab may be spaced further away from the upper lip than is shown in FIGS. 5 and 6 when the device is in the fully inserted configuration. Nonetheless, the tab 360 still facilitates maintaining the device 300 stably in the fully inserted configuration when tape is attached to the tab 360 and the patient's head as shown generally in FIG. 6.

As noted above, and as shown in FIGS. 4A, 4B, and 4D, the distal portion 420 of the connector portion 400 of the airway tube is oblong. The cross section of the integral tube and backplate portion 450 is also oblong rather than cylindrical. FIG. 4E shows a cross sectional view of the integral tube and backplate portion 450 taken along the line 4E—4E as shown in FIG. 4A. As shown in FIG. 4E, the integral tube and backplate portion is generally oblong and defines two longitudinal folds 462 that extend along the left and right sides of the airway tube. As discussed in the above-identified copending U.S. patent application Ser. Nos. 09/544,681 and 10/138,806, the longitudinal folds 462 advantageously help prevent the airway tube from collapsing, or forming a "kink", when the tube is bent so as to insert the device into a patient. As is also discussed in those copending applications, the patient's natural airway passage is generally oblong rather than cylindrical, and an oblong airway tube fits within the natural airway passage better than a cylindrical tube. Once an oblong airway tube has been positioned within a patient, the anatomical structures that define the patient's natural airway passage tend to prevent the tube from twisting, or rotating, in the direction generally indicated by the arrow R—R shown in FIG. 4E. In contrast, a device with a cylindrical airway tube rotates within the patient, in the direction indicated by the arrow R—R, much more easily.

Although the tab 360 may be used with a variety of laryngeal mask airway devices, it is most advantageously used with devices in which the cross section of the airway tube is oblong (e.g., as generally illustrated in FIG. 4E). Tape applied to the tab 360 applies force along the length of the device, or along a long axis of the device, as discussed above in connection with FIG. 6 and the oblong shape of the airway tube helps prevent the device from twisting about that axis.

Referring back to FIG. 3A, tab 360 extends from flange 430 at an angle theta ($\theta$). Once choice for the angle theta is fifteen degrees. Referring to FIG. 4C, tab 360 extends from flange 430 by a height H. Once choice for the height H of tab 360 is about fifteen millimeters. Referring to FIG. 4A, the line L is parallel to the edges of the proximal portion 410 and the distal portion 420. Flange 430 extends from the proximal and distal portions 410, 420 in directions substantially perpendicular to the line L. In particular, flange 430 extends from distal portion 420 in a direction substantially perpendicular to line L for a distance D, and then angles off, by the angle theta (as shown in FIG. 3A) to define tab 360. One choice for the distance D is five millimeters.

Another way to describe the orientation of tab 360 with respect to the airway tube is that the tab extends from the wall of the tube, which defines the tube's internal airway passage, outwardly, or away from the internal passage. When the device 300 is in the fully inserted configuration, the tab extends from the tube wall outwardly towards the patient's nose. More generally, if an up-down direction is defined as being along a line extending between the patient's nose and the patient's chin, the tab 360 extends generally in the up-down direction when the device is in the fully inserted configuration.

In addition to facilitating holding device 300 stably in the fully inserted configuration, tab 360 also facilitates insertion of device 300 into a patient and also facilitates general manipulation of the device. The proximal end of the airway tube is typically grasped and manipulated as a laryngeal mask airway device is inserted into a patient. Lubricant is typically applied to facilitate passing the mask portion through the patient's natural airway. However, the lubricant can also make the proximal end of the airway tube slippery and difficult to handle. Tab 360, which extends outwardly from the proximal end of the airway tube, provides an additional surface that may conveniently be grasped during insertion and manipulation of the device. Tab 360 thereby generally facilitates insertion and manipulation of device 300.

As discussed above, device 300 has a single tab 360 that projects generally along the patient's upper lip when the device is in the fully inserted configuration. One reason this configuration is convenient is that the patient's upper lip and cheeks are generally immobile with respect to the rest of the patient's head. In contrast, the patient's lower lip and jaw are easily moved with respect to the head and accordingly provide a less stable platform for anchoring the device 300. However, although a single tab projecting along the upper lip is a convenient configuration, it will be appreciated that other configurations of tabs may be used. For example, devices constructed according to the invention can instead include a tab that projects downward along the lower patient's lower lip, or in some other direction. Alternatively, devices constructed according to the invention can include two tabs, one projecting along the upper lip and another projecting along the lower lip, when the device is in the fully inserted configuration, and adhesive tape may be fixed to either or both of the tabs and to the patient's cheeks or to other parts of the face.

Also, provision of tabs, such as tab 360, have been discussed in the context of disposable laryngeal mask airway devices. It will be appreciated that such tabs may also be usefully included according to the invention in non-disposable laryngeal mask airway devices.

Also, tab 360 has been discussed as extending substantially perpendicularly from the distal portion 420 for a distance D and then continuing to extend at an angle theta. It will be appreciated that these are merely preferred choices and that the geometry of the tab can vary considerably. For example, the tab need not extend in a direction substantially perpendicular to a line such as line L, and the tab may instead simply extend in a direction generally transverse, or crosswise, to such a line. Also, the tab need not extend in one direction for a first distance and then continue to extend at the angle theta as shown, and may instead simply be formed, for example, as a single planar piece. However, the tab 360 preferably extends for a distance that is short enough to prevent interference with bodily structures (e.g., short enough to prevent bumping into the nose) and that is long enough to permit easy and reliable attachment of adhesive tape, such that the tape, when applied, reliably biases the tab inwards towards the patient and the tape does not easily slip off of the tab.

Figure 1A:
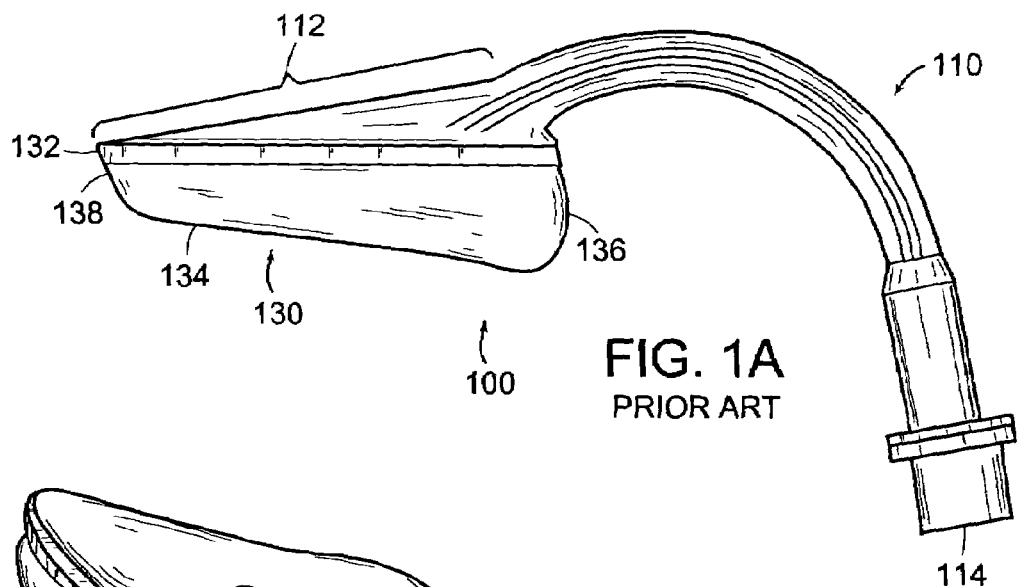
FIG. 1A shows a side view of a prior art disposable laryngeal mask airway device when the cuff is inflated.
Figure 1B:
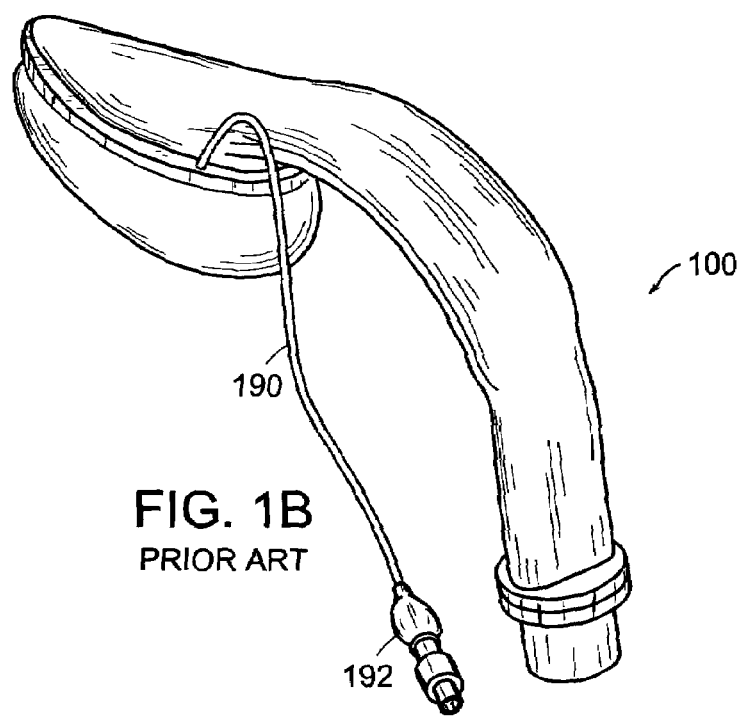
FIG. 1B shows a perspective view of the posterior side of the prior art device shown in FIG. 1A.
Figure 1C:
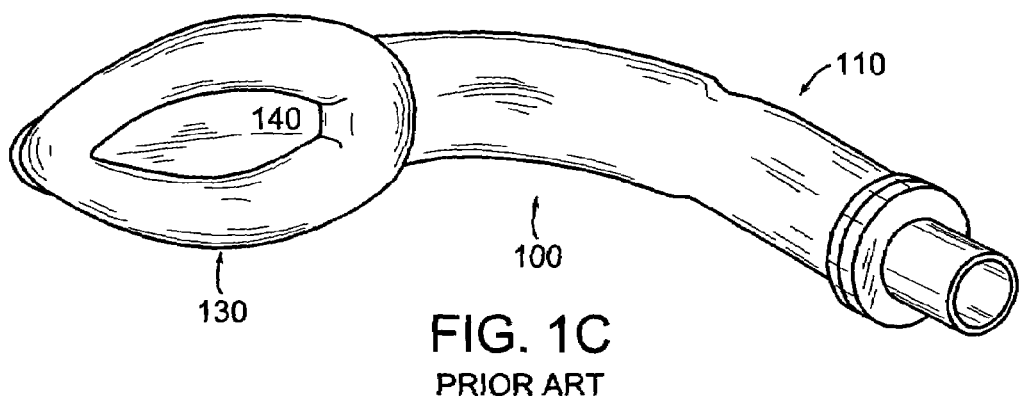
FIG. 1C shows a perspective view of the anterior side of the prior art device shown in FIG. 1A.
Figure 2:
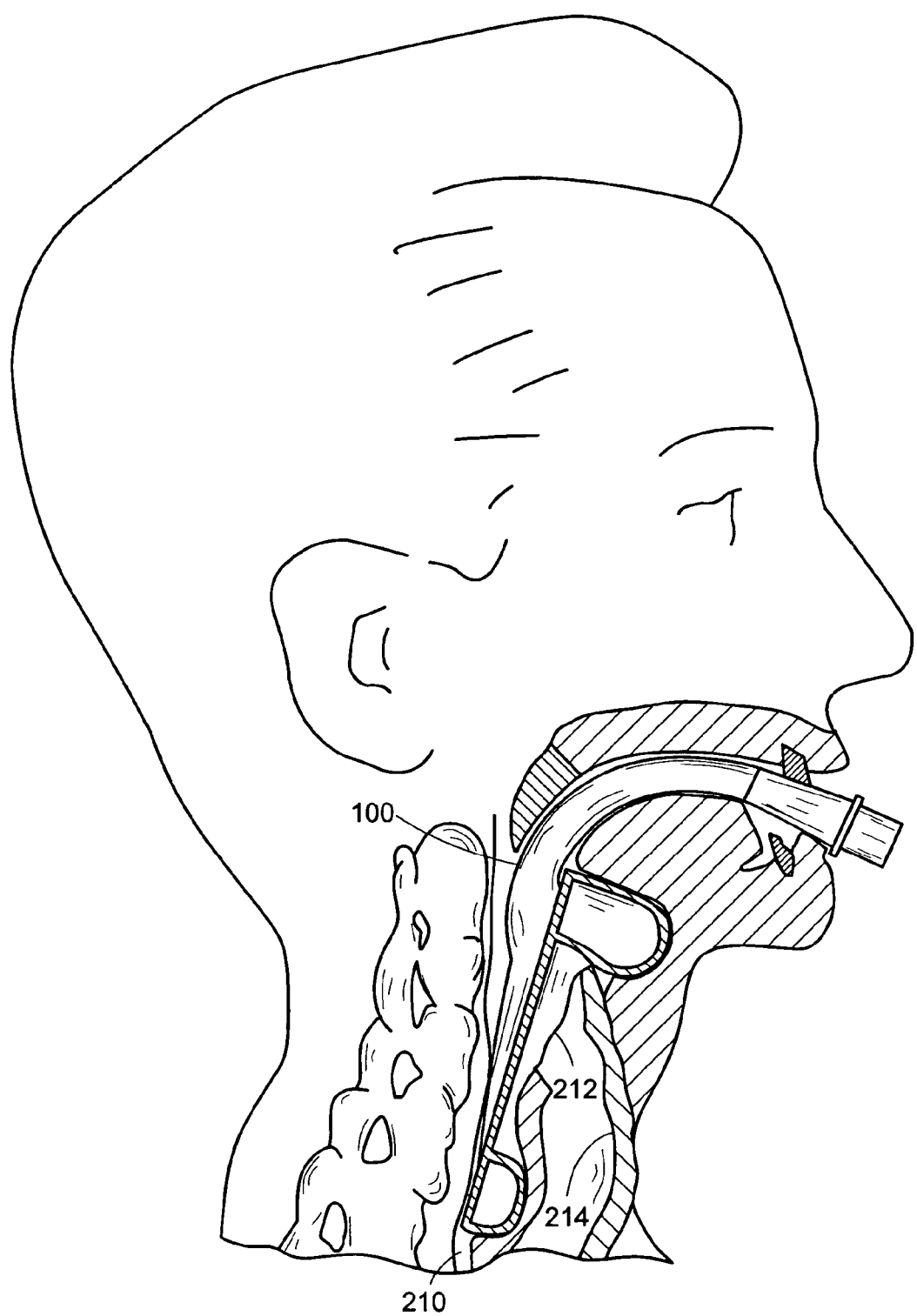
FIG. 2 shows a partially sectional side view of the device shown in FIGS. 1A–1C when the device is in the fully inserted configuration.

It will be appreciated that tab 360 differs markedly from flanges used in prior art devices, such as those illustrated in FIGS. 1A–C. Such prior art flanges did not extend from the airway tube for a sufficient length, or with a suitable geometry, to permit attachment of adhesive tape to the flange and to the patient's head in any fashion that would reliably, and stably, apply a force biasing the device into the patient. It is presently believed that the tab must extend at least about fifteen millimeters from the airway tube to permit reliable attachment of adhesive tape to the tab and to the patient's head such that the tape will reliably remain in place and continuously apply a force to the tab so as to bias the tab towards the patient's head.

Figure 7A:
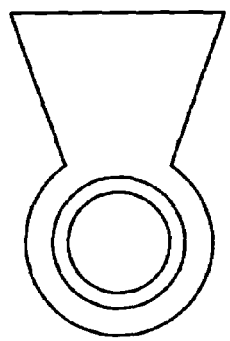
FIGS. 7A–7G show alternative configurations of tabs constructed according to the invention.
Figure 7B:
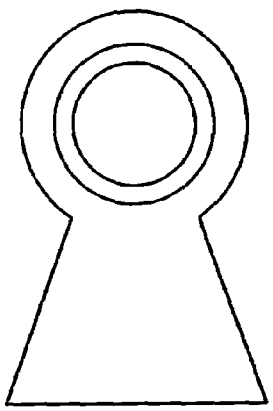
Figure 7C:
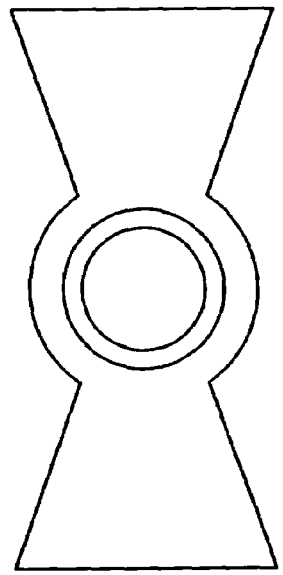
Figure 7D:
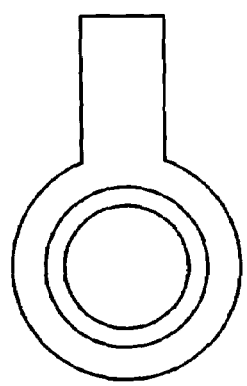
Figure 7E:
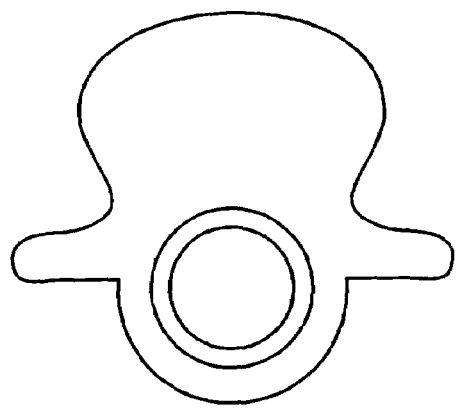
Figure 7F:
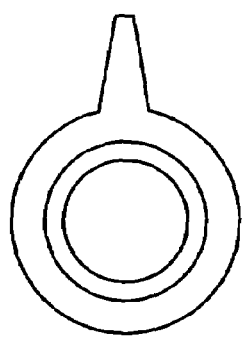
Figure 7G:
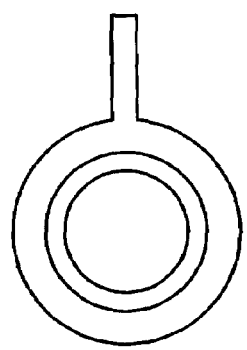

FIGS. 7A–7G show a variety of tab configurations embraced within the invention. Each of FIGS. 7A–7G is taken from an orientation similar to that of FIG. 4C. FIG. 7A shows a configuration similar to that of the tab shown in FIG. 4C (i.e., a single tab that projects upwards along the patient's upper lip when the device is in the fully inserted configuration). FIG. 7B shows a single tab configuration in which the tab projects downwards towards the patient's chin when the device is in the fully inserted configuration. FIG. 7C shows a two tab configuration in which the two tabs project upwards and downwards. FIG. 7D shows a single upwardly projecting tab in which the sides of the tab are parallel to one another instead of slanted. FIG. 7E shows a rounded tab that projects along the upper lip. The rounded tab is narrower at the base and wider at the top. If adhesive tape is attached to the base of the tab, the wider portion of the tab near the top can prevent the tape from sliding off of the tab. FIG. 7F shows a single tab configuration in which the sides of the tab slant towards a vertex above the end of the tab. The tab shown in FIG. 7F has a straight top edge. Alternatively, the top of the tab can be located at a vertex of the two slanting sides such that the top of the tab is pointed. As yet another alternative to any of the configurations shown in FIGS. 7A–7F, the edges of the tabs may be curved rather than straight. FIG. 7G shows a single tab that projects along the patient's upper lip when the device is in the fully inserted configuration. In FIG. 7G, the tab is cylindrical, or rod shaped, rather than flat.

Figure 8A:
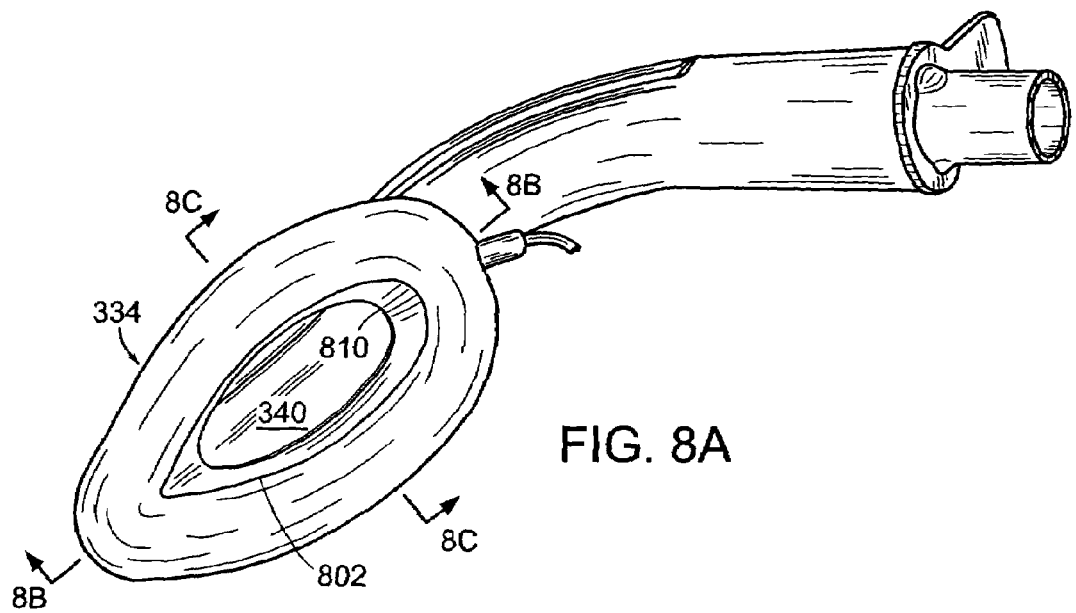
FIG. 8A shows a perspective view of the anterior side of the device shown in FIG. 3A.
Figure 8B:
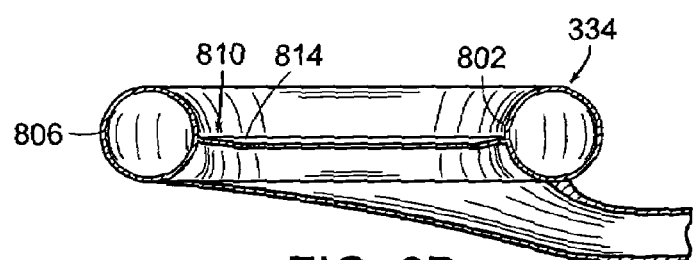
FIGS. 8B and 8C show sectional views of the device taken along the lines 8B—8B and 8C—8C, as shown in FIG. 8A.
Figure 8C:
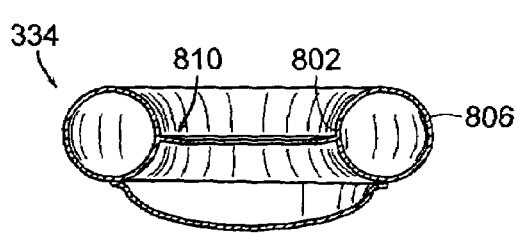

FIG. 8A shows a perspective view of the anterior side of device 300. FIGS. 8B and 8C show sectional views of device 300 taken in the direction of arrows 8B—8B and 8C—8C, respectively, as shown in FIG. 8A. FIGS. 8A–8C show the cuff 334 in detail. As shown in FIGS. 8B and 8C, the cuff 334 defines a substantially circular cross section 806, when inflated, and as shown in FIG. 8A, the cuff 334 has a generally elliptical profile. The shape of the cuff 334 is substantially similar to the cuff used in the above-identified device that is commercially marketed as the "Classic". However, unlike the cuff used in the Classic, the cuff 334 also include an epiglottis support flange 810.

Figure 8D:
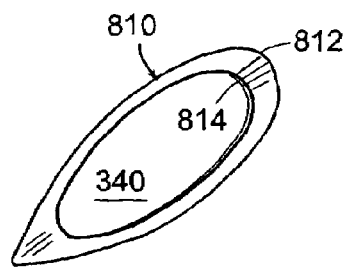
FIG. 8D shows a view of the epiglottis support flange contained within the cuff shown in FIG. 8A.

FIG. 8D shows an anterior view of epiglottis support flange 810 separated from the cuff 334. The epiglottis support flange 810 is preferably formed as an integral part of cuff 334 (e.g., by injection molding), and would not normally exist as a separate component as shown in FIG. 8D. However, the unnatural view of epiglottis support flange 810 separated from cuff 334 shown in FIG. 8D conveniently shows the shape of the flange 810. The epiglottis support flange 810 is formed from a thin ring-like sheet of material, and defines an outer perimeter 812, an inner perimeter 814, and a central aperture 340. While flange 810 is generally ring-like, it is not perfectly annular in that neither the inner perimeter 814 nor the outer perimeter 812 are circular. Rather, the inner perimeter 814 and the outer perimeter 812 are generally elliptical and match the generally elliptical profile of cuff 334. The flange 810, which is not inflatable, is joined to the inflatable portion of cuff 334.

As shown in FIGS. 8B and 8C, the inflatable portion of cuff 334 defines a circular cross section 806. The outer perimeter 812 of flange 810 is attached to an inner perimeter 802 of the inflatable portion of cuff 334. More specifically, the outer perimeter 812 of flange 810 is attached to the inflatable portion of cuff 334 at an equatorial location (i.e., half way between the top and bottom of the inflatable portion of the cuff, the orientations top and bottom being with reference to the orientation shown FIGS. 8B and 8C).

When cuff 334 is deflated, the presence of flange 810 does not add substantially to the thickness of the device. When cuff 334 is inflated, flange 810 defines a structure that can support the epiglottis when the device is in the fully inserted configuration.

Figure 9:
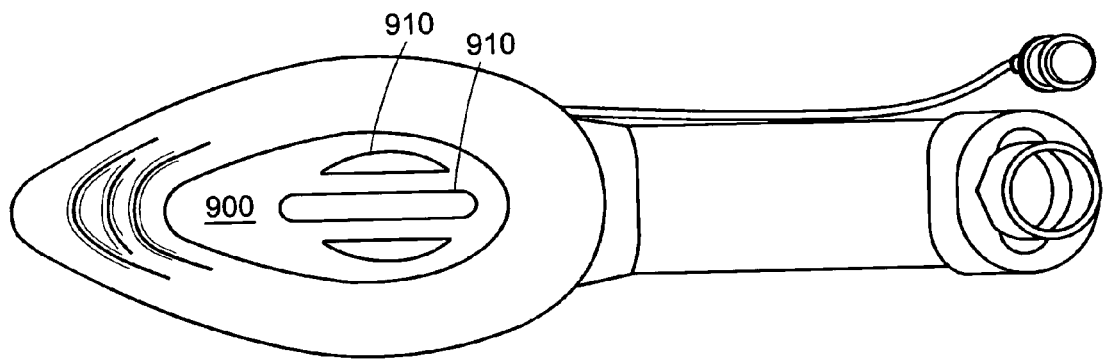
FIG. 9 shows one type of support for preventing the epiglottis from occluding the airway passage provided by a laryngeal mask airway device.

As is known, when a patient is lying in a supine position (i.e., on their back facing upwards), and when a laryngeal mask airway device is inserted in the patient, the patient's epiglottis may fall into the bowl shaped space defined (at least in part) by the inflated cuff and obstruct the airway provided by the device. Various structures have been proposed for preventing the epiglottis from so obstructing the airway. FIG. 9 shows one such structure, which consists of a sheet of material 900 that extends across the central aperture defined by the mask, and which itself defines three apertures 910. Such structures have successfully prevented the epiglottis from blocking the airway passage provided by laryngeal mask airway devices, but such structures can also be difficult to fabricate.

Figure 10:
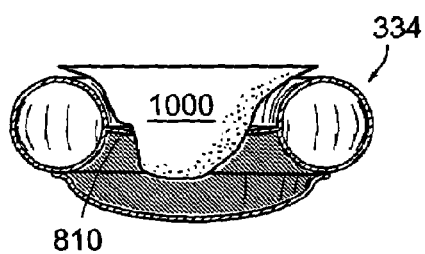
FIG. 10 shows a sectional view of the device taken from the same vantage as FIG. 8C when the device is inserted into a patient and the patient's epiglottis is falling into the bowl shaped space defined by the device.

FIG. 10 shows a cross sectional view of device 300 taken from the same orientation as FIG. 8C. However, FIG. 10 shows the device when inserted into a patient and with the patient's epiglottis 1000 falling into the bowl shape defined by the cuff 334. As shown, flange 810 supports the epiglottis 1000 and restricts the space within which the epiglottis 1000 can fall. Flange 810 generally prevents the epiglottis from falling so low as to contact the "floor" of the device, the floor being defined by the integral tube and backplate portion 450 of the airway tube 310. Most importantly, flange 810 prevents the epiglottis 1000 from obstructing the airway passage provided by the device 300, the airway passage being generally indicated by hatching in FIG. 10. Due to the oblong shape of the integral tube and backplate portion 450 of the airway tube 310, the airway passage provided by the device near the cuff is oblong (e.g., rather than cylindrical). The oblong shape of the airway passage decreases the likelihood that the epiglottis 1000 could block the passage. However, in addition to generally preventing the epiglottis 1000 from falling to the "floor" of the device and contacting the integral tube and backplate portion, the flange 810 also generally prevents the epiglottis 1000 from spreading out laterally (to the left and right, as shown in FIG. 10, towards the inflated cuff) and blocking the oblong airway passage provided by the device. Flange 810 also provides support for other anatomical structures, such as the arytenoids, that can fall into the bowl shaped space defined by the device.

When cuff 334 is inflated, the outer wall of the cuff tends to resiliently "spring" back to its original shape whenever any portion of the cuff is depressed, or biased in a particular direction (e.g., by an anatomical structure). This tendency of the cuff to resiliently spring back to its original shape is similar to the fashion in which a child's inflated balloon will return to its original shape when the balloon is squeezed and then released. Since the flange 810 is attached to cuff 334, when cuff 334 is inflated the flange 810 provides a springy, or resilient, support for anatomical structures, such as the epiglottis, that may come into contact with the flange 810.

The wall of the inflatable portion of the cuff 334 and the flange 810 may both be about 0.4 millimeters thick and may both be made of PVC material that is characterized by a durometer of about forty to fifty on the Shore A scale of hardness. The entire cuff, including flange 810 and the inflatable portion, are preferably formed simultaneously by injection molding.

As shown best in FIGS. 8B, 8C, and 10, the flange 810 preferably does not lie in a single plane. Rather, when the device is oriented as shown in FIG. 8B, the inner perimeter 814 is lower than the outer perimeter 812, and the flange is smoothly sloped between its inner and outer perimeters. This configuration helps prevent the flange 810 from presenting a sharp edge to the epiglottis 1000, should the epiglottis fall into the bowl shaped space defined by the device.

Device 300 has been disclosed as including tab 360 and epiglottis support flange 810. It will be appreciated that laryngeal mask airway devices may be constructed according to the invention that include (a) the tab but not the flange; (b) the flange but not the tab; and (c) both the tab and flange.

Figure 11:
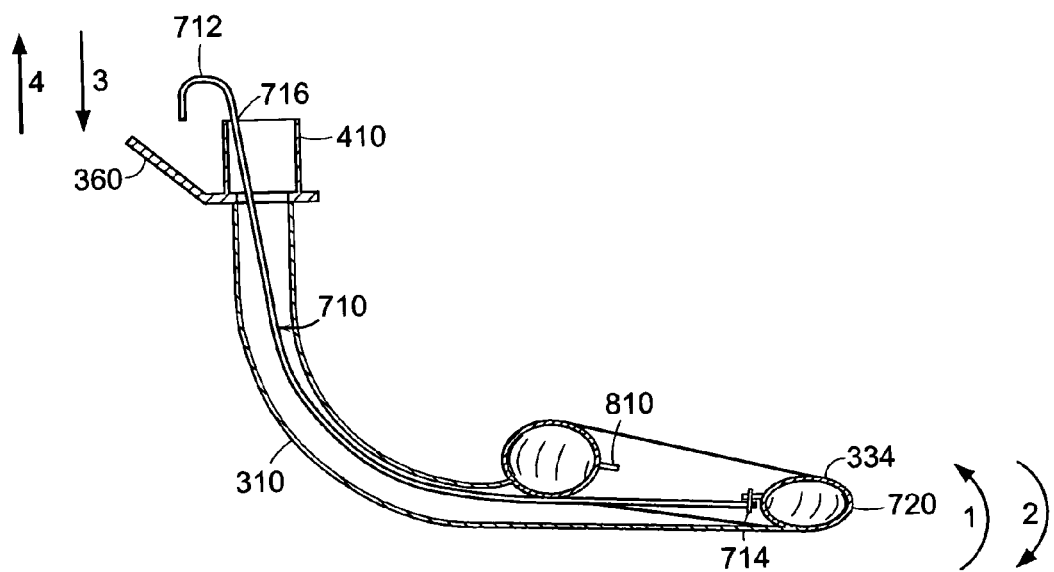
FIG. 11 shows a sectional view of another laryngeal mask airway device constructed according to the invention.

FIG. 11 shows a sectional side view of another laryngeal mask airway device 700 constructed according to the invention. Like previously discussed devices constructed according to the invention, device 700 includes airway tube 310, inflatable cuff 334, tab 360, and an epiglottis support flange 810. Device 700 also includes a rod 710. Rod 710 extends from a proximal end 712 to a distal end 714. Proximal end 712 defines a hook shape. Rod 710 extends past the connector portion 410 of the airway tube 310 such that the hook shaped proximal end 712 is disposed outside of the airway tube 310. The distal end 714 of the rod 710 is attached to or hinged to the epiglottis support flange 810. As illustrated, the distal end 714 of rod 710 is attached to the portion of the flange 810 that is closest to the distal end 720 of the device 700. Rod 710 also defines a visible indicator mark 716 near the proximal end 712. Rod 716 can be fabricated from a flexible, inelastic material such as nylon. Rod 716 can be formed as a generally flat strip that is approximately four to five millimeters wide and 0.5 to one millimeters thick. As will be discussed below, rod 710 advantageously facilitates (1) insertion of device 700 into a patient; (2) confirmation that device 700 has been properly inserted in the fully inserted configuration; and (3) detection of problems that can occur during insertion of device 700 into a patient.

Figure 12:
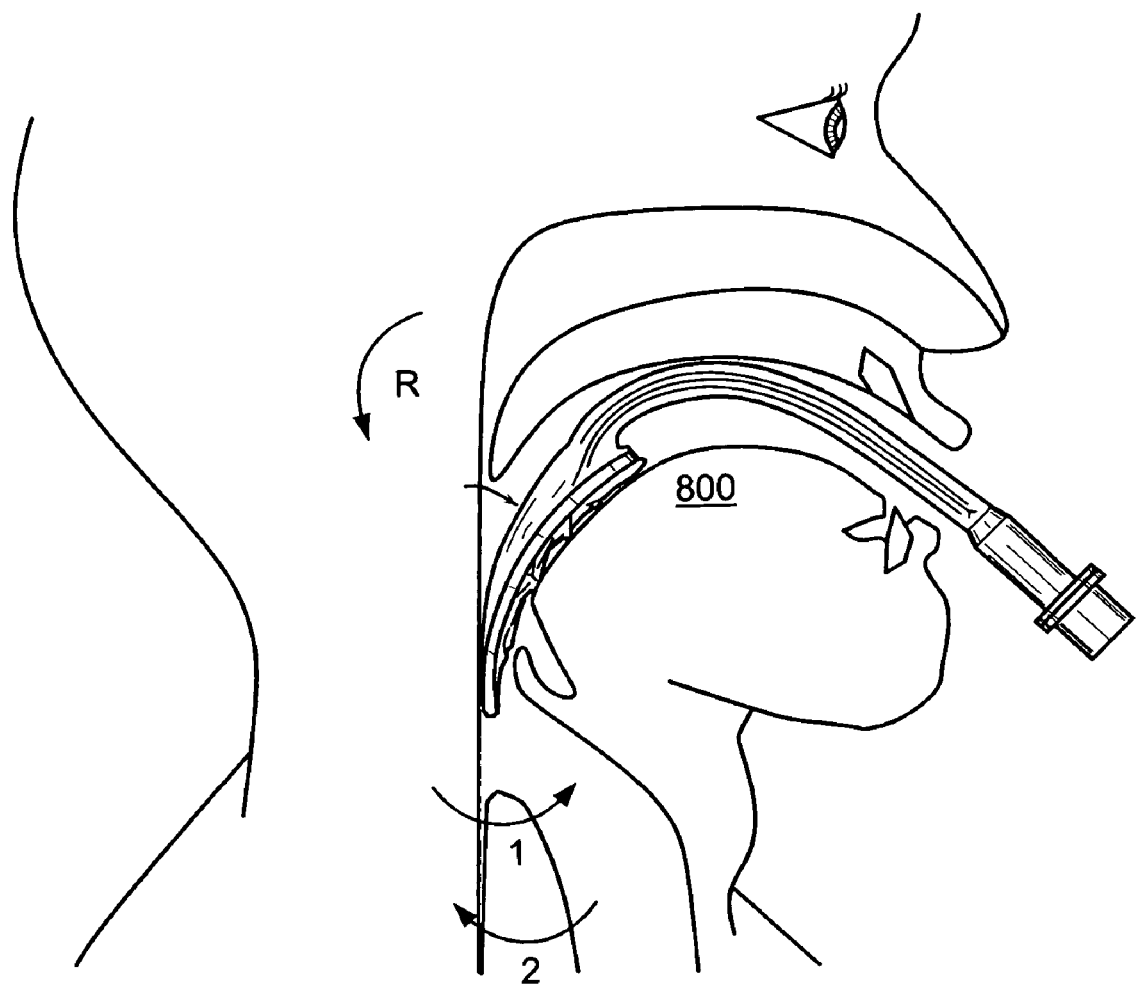
FIG. 12 shows a laryngeal mask airway device that has been partially inserted into a patient.

As discussed above, FIGS. 5 and 6 show laryngeal mask airway devices that have been placed in the fully inserted configuration. Placing such a device in the fully inserted configuration involves inserting the distal end of the device into the patient's mouth and then advancing the distal end through the patient's natural airway until the distal end is biased against the patient's normally closed esophageal sphincter. FIG. 12 shows a laryngeal mask airway device that has been partially inserted in a patient. As indicated generally in FIG. 12, during insertion, the distal end of the device temporarily curves generally in the direction indicated by the arrow R to enable the device to follow the patient's anatomical airway passage, and in particular to slide past the back of the patient's tongue 800. After temporarily curving in this direction, the device then straightens out again when it is advanced past the back of the tongue so that it can assume the profile generally illustrated in FIGS. 5 and 6.

Although the laryngeal mask airway device is generally simple to insert into a patient (e.g.,. as compared to an endotracheal tube), problems can occur during insertion. For example, instead of lodging against the esophageal sphincter, the distal end of the device sometimes enters the glottic opening such that the device extends partially into the patient's trachea. Also, the distal end of the device can become folded in the direction indicated by the arrow 1, or by the direction indicated by the arrow 2, during insertion and then fail to straighten out again such that the device never reaches the proper fully inserted configuration. Rod 700 helps detect when such undesirable conditions occur, helps prevent such undesirable conditions from occurring, and can sometimes help correct such undesirable conditions.

When device 700 is in the proper shape for allowing the device to assume the fully inserted configuration, the indicator mark 716 is adjacent to the proximal end of the connector portion 410 as shown in FIG. 11. However, if the device is bent or curved such that the distal end 720 of the device is displaced in the direction indicated by the arrow 1, the indicator mark 716 will no longer be adjacent to the proximal end of the connector portion 410 and will instead be displaced outside of the airway tube in the direction indicated by the arrow 4. Similarly, if the device is bent or curved such that the distal end 720 of the device is displaced in the direction indicated by the arrow 2, the indicator mark 716 will not be adjacent to the proximal end of the connector portion 410 and will instead be withdrawn into the airway tube in the direction indicated by the arrow 3. So, the indicator mark 716 of rod 710 can be used to detect when the device 700 is not in a proper shape for allowing the device to assume the fully inserted configuration. Such use of the indicator mark 716 allows detection of the most common problems associated with insertion of laryngeal mask airway devices.

In addition to using the rod 710 to detect the condition, or shape, of device 700, the rod 710 can also be used to control the shape of device 700. The proximal end 712 may be grasped and pushed or pulled relative to the airway tube 310 in the directions indicated by arrows 3 and 4. Pulling the proximal end 712 in the direction indicated by arrow 4 causes the distal end 720 of the device to move in the direction indicated by the arrow 1. Similarly, pushing on the proximal end 712 in the direction indicated by arrow 3 causes the distal end 720 of the device to move in the direction indicated by the arrow 2. Such motions of the rod 710 can facilitate insertion of the device into a patient. For example, pulling the rod in the direction indicated by arrow 4 can help the distal end of the device to curve around the back of the patient's tongue during insertion. Similarly, pushing on the rod in the direction indicated by arrow 3 can help straighten out the device. If it is not possible to correct the shape of the device by pulling or pushing on the rod, the position of the indicator mark 716 will indicate that the device 700 has not been properly inserted and the device can simply be withdrawn from the patient and inserted again.

In addition to the other advantageous features of tab 360 which have been discussed above, tab 360 also provides a convenient place for holding airway tube 310 while manipulating the proximal end 712 of rod 710. As discussed above, the distal end 714 of rod 710 can be attached to the epiglottis support flange 810. However, the distal end of rod 714 can alternatively be attached to the airway tube 310 itself. In such embodiments, it is generally advantageous to attach the distal end of the rod 714 to the distal most portion of the airway tube 310. Referring back to FIG. 4E, which shows a cross section of the integral tube and backplate portion 450, the portion 450 defines a notch 464 and a groove 466. As discussed in the above-identified copending U.S. patent application Ser. Nos. 09/544,681 and 10/138,806, notch 464 and groove 466 facilitate insertion of an endotracheal tube through the laryngeal mask airway device. Notch 464 and groove 466 also provide guides for rod 710 that help keep the rod 710 centered within the airway tube and help prevent the rod 710 from being displaced laterally within the airway tube.

Device 700 has been disclosed as including tab 360, epiglottis support flange 810, and rod 710. It will be appreciated that laryngeal mask airway devices may be constructed according to the invention that include the rod with or without either of the tab and flange.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A laryngeal mask airway device, comprising:
   A. an inflatable cuff, the cuff defining a central opening at least when inflated, the cuff being insertable through a mouth of a patient to an inserted location within the patient, the cuff surrounding a glottic opening of the patient when inflated and at the inserted location;
   B. an airway tube extending from a proximal end to a distal end, the airway tube defining an internal passage, a sealed airway passage extending from the proximal end of the tube through the internal passage to the glottic opening when the cuff is inflated and at the inserted location; and
   C. a tab fixed to the airway tube near the proximal end of the airway tube, the tab being disposed outside of the mouth of the patient when the cuff is at the inserted location, the tab extending outwardly from the airway tube in a first direction when the cuff is at the inserted location, a second direction being perpendicular to a line extending from a nose of the patient to a chin of the patient, the first direction being transverse to the second direction.

2. A device according to claim 1, the first direction extending from the patient's chin towards the patient's nose.

3. A device according to claim 2, the tab defining two straight side edges and a top edge, the side edges defining lines that intersect at a vertex, the top edge being between the vertex and the patient's nose when the cuff is at the inserted location.

4. A device according to claim 1, the first direction extending from the patient's nose towards the patient's chin.

5. A device according to claim 4, the tab defining two straight side edges and a bottom edge, the side edges defining lines that intersect at a vertex, the bottom edge being between the vertex and a foot of the patient when the cuff is at the inserted location.

6. A device according to claim 1, the tab being disposed near an upper lip of the patient when the cuff is at the inserted location.

7. A device according to claim 6, the tab extending from the airway tube towards a nose of the patient when the cuff is at the inserted location.

8. A device according to claim 7, the tab including a first portion and a second portion, the first portion of the tab extending outwardly from the airway tube, the second portion extending from the first portion at an angle with respect to the first portion, the angle being different than one hundred eighty degrees.

9. A device according to claim 7, the airway tube including a connector portion and a second portion, the connector portion including a proximal portion, a distal portion, and a flange, the flange being disposed between the proximal and distal portions, the distal portion being inserted into a proximal end of the second portion, the proximal portion being cylindrical.

10. A device according to claim 9, the flange defining the tab.

11. A device according to claim 1, the tab being configured to permit application of adhesive tape to the tab and a face of the patient such that the tape, when applied, biases the tab towards the mouth of the patient.

12. A device according to claim 11, the tab being configured to permit application of adhesive tape to the tab, a left cheek, and a right cheek of the patient.

13. A device according to claim 11, the adhesive tape, when applied, biasing a distal end of the device against an esophageal sphincter of the patient.

14. A device according to claim 1, the tab extending from the airway tube for at least fifteen millimeters.

15. A device according to claim 14, the tab extending from the airway tube for fifteen millimeters.

16. A device according to claim 1, the tab including a first portion and a second portion, the first portion of the tab extending outwardly from the airway tube, the second portion extending from the first portion at an angle with respect to the first portion, the angle being different than one hundred eighty degrees.

17. A device according to claim 1, the tab being substantially rigid.

18. A device according to claim 1, a cross section of the airway tube being oblong.

19. A device according to claim 1, the device further including an epiglottis support flange.

20. A device according to claim 1, the cuff defining an inner perimeter that bounds the central opening, the device further including an epiglottis support flange, the flange defining an outer perimeter and an inner perimeter, the outer perimeter of the flange being fixed to the inner perimeter of the cuff, the inner perimeter of the flange defining a second opening, the second opening being smaller than the central opening.

21. A laryngeal mask airway device, comprising:
   A. an inflatable cuff, the cuff defining a central opening at least when inflated, the cuff being insertable through a mouth of a patient to an inserted location within the patient, the cuff surrounding a glottic opening of the patient when inflated and at the inserted location; and
   B. an airway tube extending from a proximal end to a distal end, the airway tube including a tube wall that defines an internal passage, a sealed airway passage extending from the proximal end of the tube through the internal passage to the glottic opening when the cuff is inflated and at the inserted location, the airway tube defining a tab, the tab being disposed outside of the mouth of the patient when the cuff is at the inserted location, the tab extending outwardly from the tube wall in a first direction when the cuff is at the inserted location, a second direction being perpendicular to a line extending from a nose of the patient to a chin of the patient, the first direction being transverse to the second direction.

22. A device according to claim 21, the tab extending from the tube wall in the first direction sufficiently far to permit application of adhesive tape to the tab and to a head of the patient when the cuff is at the inserted location such that the adhesive tape, when applied, biases the tab towards the head of the patient.

23. A method of providing ventilation to a patient, comprising:
   A. providing a laryngeal mask airway device, comprising:
      (i) an inflatable cuff, the cuff defining a central opening at least when inflated, the cuff being insertable through a mouth of a patient to an inserted location within the patient, the cuff surrounding a glottic opening of the patient when inflated and at the inserted location; and (ii) an airway tube extending from a proximal end to a distal end, the airway tube having a tube wall that defines an internal passage, a sealed airway passage extending from the proximal end of the tube through the internal passage to the glottic opening when the cuff is inflated and at the inserted location, the airway tube defining a tab, the tab being disposed near the proximal end of the airway tube, the tab being disposed outside of the mouth of the patient when the cuff is at the inserted location, the tab extending outwardly from the tube wall in a first direction when the cuff is at the inserted location, a second direction being perpendicular to a line extending from a nose of the patient to a chin of the patient, the first direction being transverse to the second direction;

B. inserting the cuff through the mouth of the patient to the inserted location;

C. inflating the cuff;

D. applying adhesive tape to the tab and to a head of the patient such that the tape biases the tab towards the head of the patient.

24. A method according to claim 23, wherein applying adhesive tape comprises applying the tape to the tab and to a face of the patient such that the tape biases the tab towards the mouth of the patient.

25. A method according to claim 23, wherein applying adhesive tape also biases a distal end of the device against an esophageal sphincter of the patient.

26. A laryngeal mask airway device, comprising:

A. an inflatable cuff, the cuff defining a central opening at least when inflated, the cuff being insertable through a mouth of a patient to an inserted location within the patient, the cuff surrounding a glottic opening of the patient when inflated and at the inserted location;

B. an airway tube extending from a proximal end to a distal end, the airway tube defining an internal passage, a sealed airway passage extending from the proximal end of the tube through the internal passage to the glottic opening when the cuff is inflated and at the inserted location;

C. a flange fixed to the airway tube near the proximal end of the airway tube, the flange being disposed outside of the mouth of the patient when the cuff is at the inserted location, the flange including a first portion and a second portion, the first portion of the flange extending in a first direction outwardly from the tube, the second portion extending from the first portion at an angle with respect to the first portion, the angle being different than one hundred eighty degrees.

27. A laryngeal mask airway device, comprising:

A. an airway tube extending from a proximal end to a distal end, the airway tube defining an internal passage;

B. an inflatable cuff, the cuff defining a central opening at least when inflated, the cuff being disposed near the distal end of the airway tube, the cuff being insertable through a mouth of a patient to an inserted location within the patient, the cuff surrounding a glottic opening of the patient when inflated and at the inserted location, a sealed airway passage extending from the proximal end of the tube through the internal passage to the glottic opening when the cuff is inflated and at the inserted location, the cuff defining an inner perimeter that bounds the central opening; and C. an epiglottis support flange, the flange defining an outer perimeter and an inner perimeter, the flange comprising a solid sheet of material extending between the outer and inner perimeters of the flange, the outer perimeter of the flange being fixed to the inner perimeter of the cuff, the inner perimeter of the flange defining a single opening, the single opening being smaller than the central opening.

28. A device according to claim 27, the epiglottis support flange being part of the cuff.

29. A device according to claim 27, the device further including a tab fixed to the airway tube near the proximal end of the airway tube, the tab being disposed outside of the mouth of the patient when the cuff is at the inserted location, the tab extending outwardly from the airway tube in a first direction when the cuff is at the inserted location, a second direction being perpendicular to a line extending from a nose of the patient to a chin of the patient, the first direction being transverse to the second direction.

30. A device according to claim 29, a cross section of the airway tube being oblong.

* * * * *